(12) United States Patent
Rotem

(10) Patent No.: US 11,013,855 B2
(45) Date of Patent: *May 25, 2021

(54) FLUID-CONNECTION MECHANISM AND METHODS FOR PATCH-PUMPS

(71) Applicant: SteadyMed Ltd., Rehovot (IL)

(72) Inventor: Nir Rotem, Gedera (IL)

(73) Assignee: STEADYMED LTD., Tel Aviv (IL)

( * ) Notice: Subject to any disclaimer, the term of this patent is extended or adjusted under 35 U.S.C. 154(b) by 115 days.

This patent is subject to a terminal disclaimer.

(21) Appl. No.: 16/377,992

(22) Filed: Apr. 8, 2019

(65) Prior Publication Data

US 2019/0231974 A1 Aug. 1, 2019

Related U.S. Application Data

(63) Continuation of application No. 15/605,420, filed on May 25, 2017, now Pat. No. 10,335,542, which is a (Continued)

(51) Int. Cl.
*A61M 5/142* (2006.01)
*A61M 5/158* (2006.01)
(Continued)

(52) U.S. Cl.
CPC ........ *A61M 5/14248* (2013.01); *A61M 5/145* (2013.01); *A61M 5/158* (2013.01);
(Continued)

(58) Field of Classification Search
CPC ...... A61M 5/142; A61M 5/162; A61M 5/145; A61M 5/14248; A61M 5/158;
(Continued)

(56) References Cited

U.S. PATENT DOCUMENTS

| 4,843,598 A | 6/1989 | Medlin |
| 4,886,514 A | 12/1989 | Maget |

(Continued)

FOREIGN PATENT DOCUMENTS

| CA | 2812877 A1 | 4/2012 |
| DE | 3621846 A1 | 1/1988 |

(Continued)

OTHER PUBLICATIONS

Lee et al., "Battery Dimensional Changes Occuring During Charge/Discharge Cycles—Thin Rectangular Lithium Ion and Polymer Cells," Journal of Power Sources, 119-121: 833-837 (2003).

*Primary Examiner* — Tiffany Legette
(74) *Attorney, Agent, or Firm* — Kilpatrick Townsend & Stockton LLP

(57) ABSTRACT

Embodiments may include a method of delivering a drug. The method may include removing or releasing a structure from a patch-pump assembly. The patch-pump assembly may include a sealed prefilled drug-reservoir, a fluid passageway, a cannula-containing assembly, and a penetrator. The method may also include penetrating the sealed prefilled drug-reservoir containing the drug to establish fluid communication between the sealed prefilled drug-reservoir and a fluid passageway by removing or releasing the structure. The method may further include flowing the drug from the prefilled drug-reservoir to the fluid passageway. In addition, the method may include flowing the drug from the fluid passageway to a cannula-containing assembly. Furthermore, the method may include delivering the drug subcutaneously to a subject using the cannula-containing assembly.

12 Claims, 9 Drawing Sheets

Figure 1B:
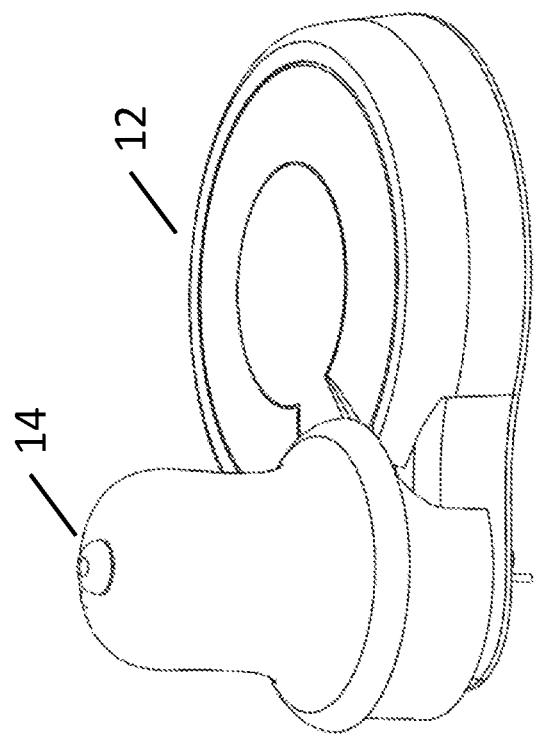

Related U.S. Application Data continuation of application No. 14/384,152, filed as application No. PCT/IL2013/050240 on Mar. 14, 2013, now Pat. No. 9,724,462.

(60) Provisional application No. 61/612,436, filed on Mar. 19, 2012.

(51) Int. Cl.
*A61M 5/145* (2006.01)
*A61M 5/162* (2006.01)

(52) U.S. Cl.
CPC . *A61M 5/1626* (2013.01); *A61M 2005/14252* (2013.01); *A61M 2005/1585* (2013.01); *F04C 2270/041* (2013.01)

(58) Field of Classification Search
CPC ........ A61M 5/1626; A61M 2005/1585; A61M 2005/14252
See application file for complete search history.

(56) References Cited

U.S. PATENT DOCUMENTS

| | | | |
|---|---|---|---|
| 5,062,834 A | 11/1991 | Gross et al. | |
| 5,102,389 A | 4/1992 | Hauser et al. | |
| 5,108,852 A | 4/1992 | Tomantschger et al. | |
| 5,109,850 A | 5/1992 | Blanco et al. | |
| 5,134,046 A | 7/1992 | Chow et al. | |
| 5,318,557 A | 6/1994 | Gross | |
| 5,354,264 A | 10/1994 | Bae et al. | |
| 5,436,372 A | 7/1995 | Yoshida et al. | |
| 5,438,249 A | 8/1995 | Chang et al. | |
| 5,505,706 A | 4/1996 | Maus et al. | |
| 5,527,288 A | 6/1996 | Gross et al. | |
| 5,563,004 A | 10/1996 | Buzzelli et al. | |
| 5,643,207 A | 7/1997 | Rise | |
| 5,677,083 A | 10/1997 | Tomiyama | |
| 5,814,020 A | 9/1998 | Gross | |
| 5,827,233 A | 10/1998 | Futagawa et al. | |
| 5,848,991 A | 12/1998 | Gross et al. | |
| 5,938,640 A | 8/1999 | Maget et al. | |
| 5,980,741 A | 11/1999 | Schnell et al. | |
| 6,150,053 A | 11/2000 | Murata et al. | |
| 6,186,982 B1 | 2/2001 | Gross et al. | |
| 6,296,967 B1 | 10/2001 | Jacobs et al. | |
| 6,312,409 B1 | 11/2001 | Gross | |
| 6,322,532 B1 | 11/2001 | D'Sa et al. | |
| 6,358,239 B1 | 3/2002 | Rake et al. | |
| 6,377,848 B1 | 4/2002 | Garde et al. | |
| 6,400,489 B1 | 6/2002 | Suzuki et al. | |
| 6,465,125 B1 | 10/2002 | Takami et al. | |
| 6,506,520 B1 | 1/2003 | Inoue et al. | |
| 6,534,218 B1 | 3/2003 | Okada et al. | |
| 6,537,249 B2 | 3/2003 | Kriesell et al. | |
| 6,537,250 B1 | 3/2003 | Kriesel | |
| 6,577,039 B2 | 6/2003 | Ishida et al. | |
| 6,589,229 B1 | 7/2003 | Connelly et al. | |
| 6,733,485 B1 | 5/2004 | Whitehurst et al. | |
| 6,982,514 B1 | 1/2006 | Lu et al. | |
| 7,242,134 B2 | 7/2007 | Wallace et al. | |
| 7,364,568 B2 | 4/2008 | Angel et al. | |
| 7,541,715 B2 | 6/2009 | Chiang et al. | |
| 8,834,454 B2 | 9/2014 | Genosar et al. | |
| 9,011,376 B2 | 4/2015 | Goldstein | |
| 9,724,462 B2 | 8/2017 | Rotem | |
| 10,335,542 B2 | 7/2019 | Rotem | |
| 2002/0107480 A1 | 8/2002 | Kriesel et al. | |
| 2002/0156461 A1 | 10/2002 | Joshi | |
| 2002/0169439 A1 | 11/2002 | Flaherty | |
| 2003/0014014 A1 | 1/2003 | Nitzan | |
| 2003/0205582 A1 | 11/2003 | Joshi et al. | |
| 2004/0059282 A1 | 3/2004 | Flock et al. | |
| 2004/0068224 A1 | 4/2004 | Couvillon et al. | |
| 2004/0115068 A1 | 6/2004 | Hansen et al. | |
| 2004/0115523 A1 | 6/2004 | Hommura et al. | |
| 2004/0115530 A1 | 6/2004 | Maeda et al. | |
| 2004/0138612 A1* | 7/2004 | Shermer | A61M 5/142 604/93.01 |
| 2005/0096587 A1 | 5/2005 | Santini et al. | |
| 2006/0052768 A1 | 3/2006 | Joshi et al. | |
| 2006/0069344 A1 | 3/2006 | Southam et al. | |
| 2006/0102455 A1 | 5/2006 | Chiang et al. | |
| 2006/0106346 A1 | 5/2006 | Sullivan et al. | |
| 2006/0200073 A1 | 9/2006 | Radmer et al. | |
| 2006/0229998 A1 | 10/2006 | Harrison et al. | |
| 2008/0188779 A1 | 8/2008 | Vallero | |
| 2008/0248815 A1 | 10/2008 | Busch | |
| 2008/0281270 A1 | 11/2008 | Cross et al. | |
| 2009/0045251 A1 | 2/2009 | Jaiswal | |
| 2009/0069746 A1 | 3/2009 | Miller et al. | |
| 2009/0093772 A1 | 4/2009 | Genosar et al. | |
| 2009/0150294 A1 | 6/2009 | March | |
| 2009/0171842 A1 | 7/2009 | Blythe | |
| 2009/0312706 A1 | 12/2009 | Shantha et al. | |
| 2010/0022992 A1 | 1/2010 | Genosar et al. | |
| 2010/0056874 A1 | 3/2010 | Dijksman | |
| 2010/0130931 A1 | 5/2010 | Yodfat | |
| 2010/0152658 A1 | 7/2010 | Hanson et al. | |
| 2010/0266638 A1 | 10/2010 | Turkel et al. | |
| 2010/0274221 A1 | 10/2010 | Sigg et al. | |
| 2011/0047075 A1 | 2/2011 | Fourez | |
| 2011/0098652 A1 | 4/2011 | Haster et al. | |
| 2011/0160655 A1 | 6/2011 | Hanson et al. | |
| 2011/0191244 A1 | 8/2011 | Dai | |
| 2011/0276479 A1 | 11/2011 | Thomas | |
| 2011/0306929 A1* | 12/2011 | Levesque | A61M 5/1684 604/150 |
| 2012/0041338 A1 | 2/2012 | Chickering, III | |
| 2012/0042517 A1 | 2/2012 | Tronnes et al. | |
| 2012/0238849 A1 | 9/2012 | Holtzclaw et al. | |
| 2014/0148761 A1 | 5/2014 | Rotem et al. | |
| 2014/0163339 A1 | 6/2014 | Goldstein et al. | |
| 2014/0171867 A1 | 6/2014 | Walsh et al. | |
| 2015/0017493 A1 | 1/2015 | Genosar et al. | |
| 2015/0038907 A1 | 2/2015 | Rotem | |
| 2015/0045718 A1 | 2/2015 | Shlomo et al. | |
| 2016/0361491 A1 | 12/2016 | Shaked et al. | |
| 2017/0304532 A1 | 10/2017 | Rotem | |
| 2018/0035935 A1 | 2/2018 | Goldstein et al. | |

FOREIGN PATENT DOCUMENTS

| | | |
|---|---|---|
| DE | 19809483 A1 | 9/1999 |
| EP | 0676214 A1 | 10/1995 |
| EP | 1912690 A1 | 4/2008 |
| EP | 2621558 A1 | 8/2013 |
| EP | 2825225 A1 | 1/2015 |
| EP | 2827923 A1 | 1/2015 |
| GB | 2221394 A | 2/1990 |
| IL | 169807 | 2/2006 |
| JP | 02-131376 A | 5/1990 |
| JP | 04-127885 A | 4/1992 |
| WO | 97/010012 A1 | 3/1997 |
| WO | 2001/021234 A1 | 3/2001 |
| WO | 01-51108 A1 | 7/2001 |
| WO | 2002/069935 A1 | 9/2002 |
| WO | 2004/067066 A1 | 2/2003 |
| WO | 2004/006982 A2 | 1/2004 |
| WO | 2005/124918 A2 | 12/2005 |
| WO | 2007/010522 A1 | 1/2007 |
| WO | 2007/129317 A1 | 11/2007 |
| WO | 2008/-62335 A1 | 5/2008 |
| WO | 2008/122983 A1 | 10/2008 |
| WO | 2011/075100 A1 | 6/2011 |
| WO | 2012/042517 A1 | 4/2012 |
| WO | 2013/136327 A1 | 9/2013 |
| WO | 2013/140395 A1 | 9/2013 |

* cited by examiner

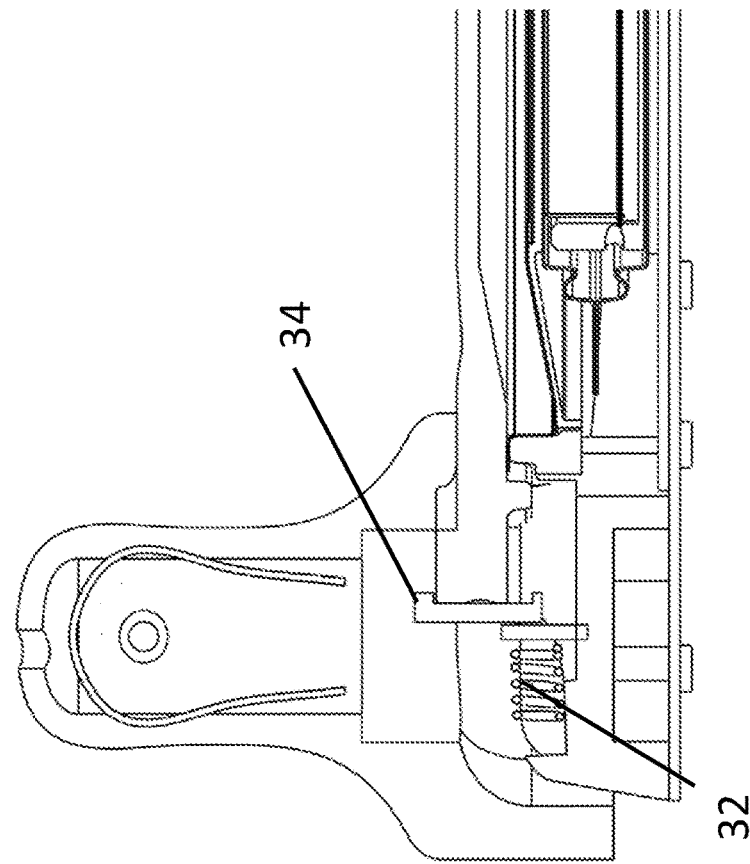
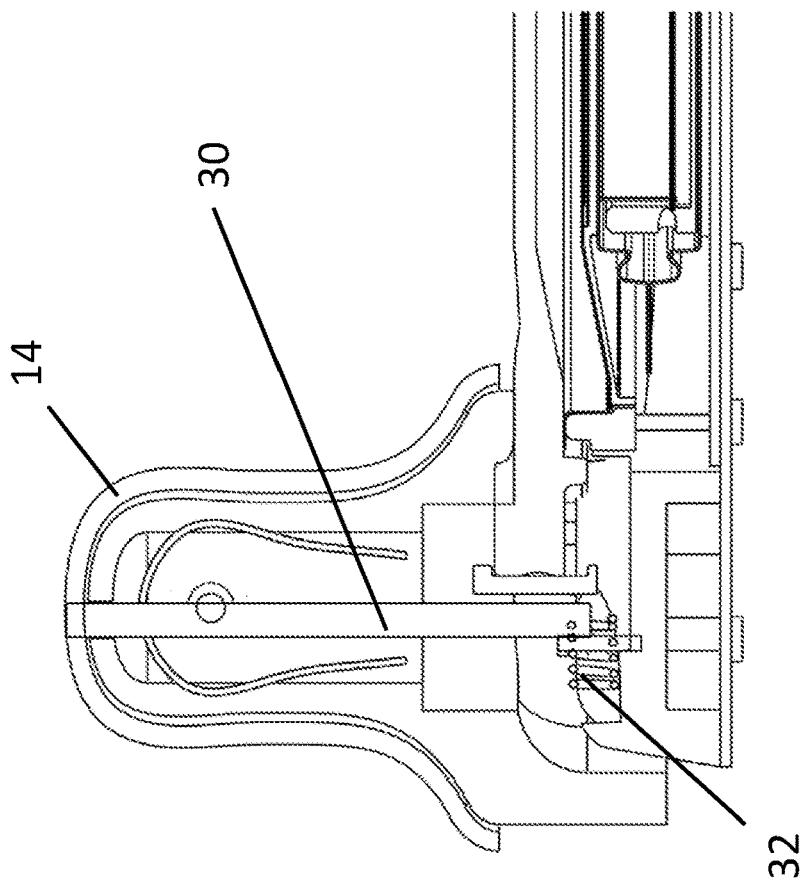

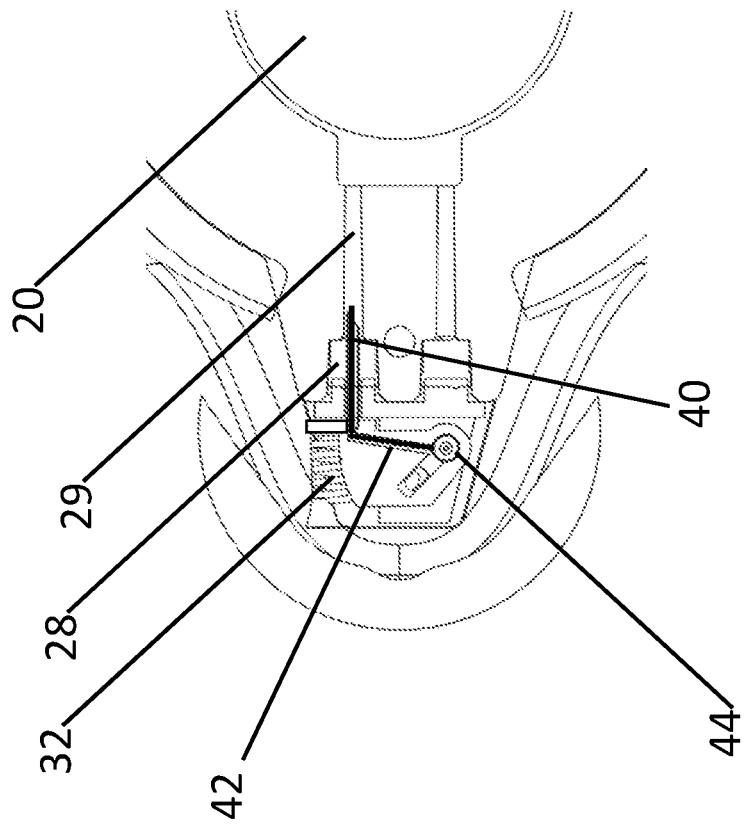
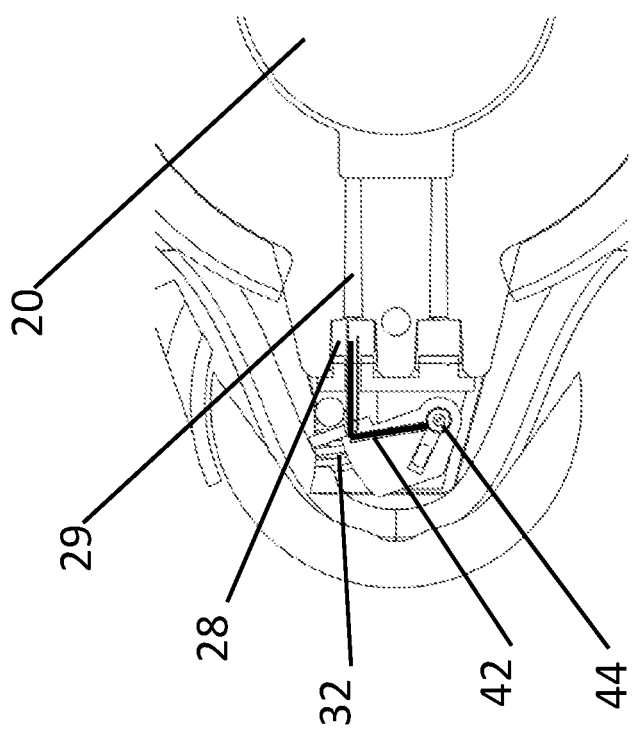
FIG. 4b
FIG. 4a

FLUID-CONNECTION MECHANISM AND METHODS FOR PATCH-PUMPS

CROSS-REFERENCES TO RELATED APPLICATIONS

This application is a continuation of U.S. patent. Ser. No. 15/605,420, filed May 25, 2017, entitled "FLUID-CONNECTION MECHANISM AND METHOD FOR PATCH-PUMPS," which is a continuation of U.S. patent application Ser. No. 14/384,152, filed Mar. 14, 2013, entitled "FLUID-CONNECTION MECHANISM FOR PATCH-PUMPS," which is a 35 U.S.C. § 371 U.S. National Stage Entry of PCT International Patent Application No. PCT/IL2013/050240 (WO 2013/140395) filed on Mar. 14, 2013, entitled "FLUID-CONNECTION MECHANISM FOR PATCH-PUMPS," which claims priority to U.S. Provisional Application No. 61/612,436, filed on Mar. 19, 2012, entitled "FLUID-CONNECTION MECHANISM FOR PRE-FILLED PATCH-PUMPS," each of which is incorporated herein by reference in its entirety.

FIELD OF THE INVENTION

The present invention is in the field of patch-pumps having a primary-container, said primary-container storing the drug to be delivered. In particular, the present invention addresses the creation of a fluid connection between said primary-container and a cannula assembly associated with said patch-pump. In some aspects, the present invention is particularly suitable for prefilled patch-pump application.

BACKGROUND OF THE INVENTION

Infusion pumps are used for treating a number of disease states requiring subcutaneous delivery of a drug. As part of the current trend towards enhanced usability, some infusion pumps are now being produced as "patch-pumps", meaning that the long tube between a remote pump and the infusion-set on the skin is eliminated. Instead, a device with a similar footprint to the infusion-set alone constitutes the entire pump, including the drug-reservoir and the actuator which drives the drug infusion. However, even though this transition to patch-pumps represents a miniaturization of the product, typically the filling process by which the patient fills the drug reservoir remains the same and is performed at the point-of-use. Other approaches for providing the drug in a patch-pump are (a) inserting a cartridge containing the drug into the patch-pump, and (b) having a pre-filled drug reservoir integrally contained within the patch-pump already during the pump manufacturing process; said drug-reservoir thereby constituting the primary-container for the drug. Whereas the act of inserting a cartridge-type reservoir into the patch-pump can open a liquid channel from the cartridge to the cannula assembly, for a drug-reservoir that is assembled within the patch-pump, an alternative means of creating this fluid connection is required.

OBJECTS OF THE INVENTION

Thus the objective of the present invention is to enable a fluid connection to be created between an integral, optionally pre-filled drug-reservoir within a patch-pump and the cannula insertion assembly associated with said patch-pump.

It is a further object of the invention to ensure that the pre-filled drug-reservoir remains sealed or that a sterile unit containing such drug reservoir be maintained as such, until directly before the activation of the patch-pump, such that the only materials that come in contact with the drug are the plastic and/or glass from which the reservoir is fabricated and one or more septa.

It is a still further object of the invention to open said fluid connection while keeping the operation of said patch-pump as simple as possible and requiring a small number of activation-steps.

SUMMARY OF THE INVENTION

The core element therefore of the present invention is a mechanism and method for exploiting one of the activation-steps required to initiate the operation of a patch-pump to create a fluid connection between the pre-filled drug reservoir assembly of said patch-pump and the cannula assembly associated with said patch-pump.

The cannula assembly of a patch-pump may be associated with the patch-pump in a number of different ways: (a) fully integrated, in which case said cannula assembly is integrated within the housing of the patch-pump, as per the OmniPod product from Insulet Inc. (MA, USA); (b) external, in which case a short tube extends from the patch-pump to a small infusion set directly adjacent to (or sharing an adhesive pad with) the patch-pump; or (c) attached to, and preferably also detachable from, the housing of the patch-pump as per the preferred embodiment detailed below.

The present invention describes the automatic opening of a liquid channel between a sealed pre-filled drug-reservoir and said cannula assembly as a result of one of the activation-steps undertaken when starting the patch-pump. Such steps typically include placing the patch-pump on the skin of the patient, removing a safety catch, or pressing a button which causes the cannula to be inserted or activates the actuator of said patch-pump. According to the present invention, the performance or one or more of these activation-steps will cause the automatic opening of a fluid channel between the pre-filled reservoir and the cannula assembly without a dedicated step being required for this purpose. Advantageously, this simplifies the use of the patch-pump while simultaneously ensuring that the pump cannot be activated in a state in which it is only later determined that the pre-filled reservoir remains sealed.

In one embodiment, said opening of the fluid channel is performed automatically either on the step of removing a safety catch or cover, or a step of activating the cannula insertion.

In some embodiments, this invention provides a selectively activatable patch-pump assembly, said patch-pump assembly comprising:

a sealed prefilled drug-reservoir containing a drug to be delivered;

an associated conduit in connection therewith;

a selectively activatable penetrator which penetrates said sealed prefilled drug-reservoir and facilitates drug access to said conduit; and a selectively activatable associated cannula-containing assembly for delivering a drug subcutaneously to a subject, in fluid connection with said conduit;

wherein a selective activation-step initiates penetration of said sealed prefilled drug-reservoir, drug access from said drug-reservoir to said conduit, drug access from said conduit to said cannula-containing assembly and delivery from said cannula-containing assembly, thereby being a selectively activatable patch-pump assembly.

According to this aspect, and as referred to herein the term "selectively activatable" is to be understood to refer to a requirement for an activation step, i.e., a specific action to be taken to produce the outcome. For example, and representing some embodiments, the term "selectively activatable patch-pump assembly" is to be understood to encompass an assembly whose delivery of the drug via known patch-pump mechanisms, is regulated such that an activation step is required or delivery from the patch pump is prevented.

Similarly, the term "selectively activatable penetrator", relates to a penetrator mechanism which penetrates a prefilled drug-reservoir and does so in a selective manner, thereby preventing spontaneous rupture of such reservoir.

Similarly, the term "selectively activatable associated cannula-containing assembly", relates to an assembly which provides for delivery of a drug subcutaneously to a subject, and does so in a selective manner, thereby preventing spontaneous subcutaneous puncture of the subject.

It is to be understood that the invention provides a number of devices, which uniquely regulate coordinated activation steps for the selective penetration of a drug reservoir releasing such drug-containing contents into a proximal conduit, which conduit is selectively put into contact with an access port in a cannula-containing assembly, regulating delivery of such drug-containing contents subcutaneously to said subject.

In some embodiments, the selectively activatable penetrator comprises a hypodermic needle. In other embodiments, the selectively activatable penetrator comprises any appropriate structure capable of penetrating the drug reservoir in a controllable manner.

The sealed prefilled drug-reservoir containing a drug to be delivered is located proximally, and is associated with a conduit in connection therewith. It will be appreciated that the conduit may be of any suitable material, size and geometry to suit a particular device.

The conduit, in turn, may contain, or at least partially include therewithin a selectively activatable penetrator which penetrates said sealed prefilled drug-reservoir and facilitates drug access to said conduit. In some embodiments, such conduit may contain a septum, which prevents access of the outside environment to said drug reservoir, thereby maintaining a sterile environment for said drug reservoir.

In some embodiments, the selectively activatable penetrator is located within the conduit and is located minimally or partially within the septum, providing easier access to such drug reservoir upon activation thereof.

The selectively activatable associated cannula-containing assembly is located in fluid connection with the conduit.

According to this aspect, and in some embodiments, the cannula-containing assembly provides for the delivery of the drug-containing substance liberated from the drug reservoir. In some embodiments, such cannula-containing assembly comprises a part capable of piercing the skin. In some embodiments, such cannula-containing assembly may resemble a venicath or similar structure, which provides for skin puncture to promote subcutaneous delivery. In some embodiments, such catheter-containing part may be flexible or rigid.

A selective activation-step initiates penetration of said sealed prefilled drug-reservoir, drug access from said drug-reservoir to said conduit, drug access from said conduit to said cannula-containing assembly and delivery from the cannula-containing assembly.

In some embodiments, the selectively activatable patch-pump assembly mechanism further comprises a safety catch or cover preventing the inadvertent activation of the patch-pump.

According to this aspect, and in some embodiments, such safety catch may comprise a pin, or slot, or other structure, which locks or otherwise prevents the penetrating member from penetrating the drug reservoir, and or prevents the cannula-containing assembly from advancing within said patch pump assembly and initiating subcutaneous delivery.

In some embodiments, removal or release of a safety catch or a cover, or a combination thereof, comprises the activation-step which initiates penetration of the sealed prefilled drug-reservoir and facilitates drug access to the conduit.

In some embodiments, the selectively activatable patch-pump assembly further comprises a first spring-based mechanism, which propels the selectively activatable penetrator through the conduit and in some embodiments, through the septum, toward the sealed prefilled drug-reservoir, thereby facilitating penetration of the drug-reservoir.

In some embodiments, the selectively activatable patch-pump assembly further comprises a second spring-based mechanism, which propels the cannula-containing assembly toward proximally located skin following drug access to the conduit.

In some embodiments, the cannula-containing assembly comprises an access port, which access port is alignable with the conduit in a selective manner. In some embodiments, only activation, for example by depressing a button on a top or side of such device, results in controlled propelling of the cannula-containing assembly toward the skin of a wearer thereof, whereby an access port in such cannula-containing assembly is only aligned with the conduit when propelled sufficiently toward the skin of the subject.

In some embodiments, the selectively activatable patch-pump assembly further comprises an actuator which compresses said prefilled drug-reservoir following penetration of said sealed prefilled drug-reservoir.

Such actuator and arrangement may comprise any known means, and in some embodiments, specifically contemplates a drug delivery actuator such as that described in United States Patent Application Publication Number US 2009-0093772, fully incorporated by reference herein and United States Patent Application Publication Number US 2010-0022992, fully incorporated by reference herein.

In some embodiments, the selectively activatable patch-pump assembly is a single unit.

In some embodiments, the selectively activatable patch-pump assembly is comprised of operationally connectable units comprised of a drug reservoir-containing unit and a cannula-containing assembly.

From a user-convenience perspective, the less number of activation-steps used the better. However, in order to minimize the chance of inadvertent activation, it is wise to also have a safety catch or cover. Thus, in the present invention, it is immaterial whether the activation-step which opens up the fluid channel between the prefilled-reservoir and the cannula assembly is the safety catch step or the cannula-insertion one.

In a further embodiment, the cannula insertion also activates the actuator of the patch-pump, such that the number of activation-steps is reduced to the lowest practical minimum, thereby enhancing simplicity while improving patient compliance.

In another embodiment of the approach in which removing the safety catch (or safety cover) opens said fluid channel, removal of said catch releases a spring-loaded hollow penetrating-member to penetrate through a septum of said drug-reservoir, said penetrating-member then serving as a fluid conduit towards the cannula assembly. In this way, the drug-reservoir remains sealed until just before use.

In another embodiment, the conduit leads to a passageway which interfaces with the cannula assembly, such that when the cannula is inserted into the skin said passageway is then placed in fluid connection with said cannula.

According to this aspect, the fluid connection from the prefilled drug-reservoir to the cannula is completed. Note that said cannula assembly may employ either a soft-cannula or a rigid-cannula.

Some embodied contemplated devices are explained more fully below, in connection with the figures, but the same shall not be construed as limiting the invention.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

FIGURES

Figure 1A:
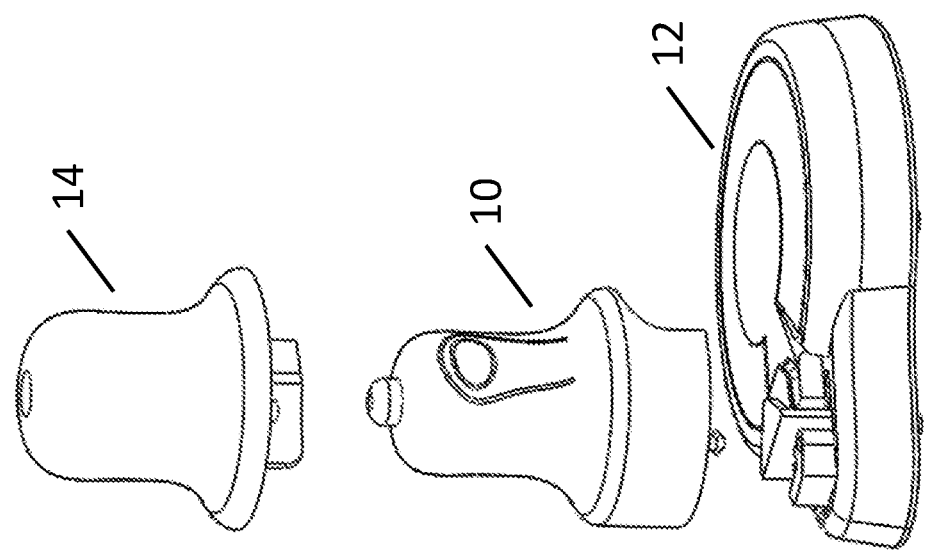
Figure 2:
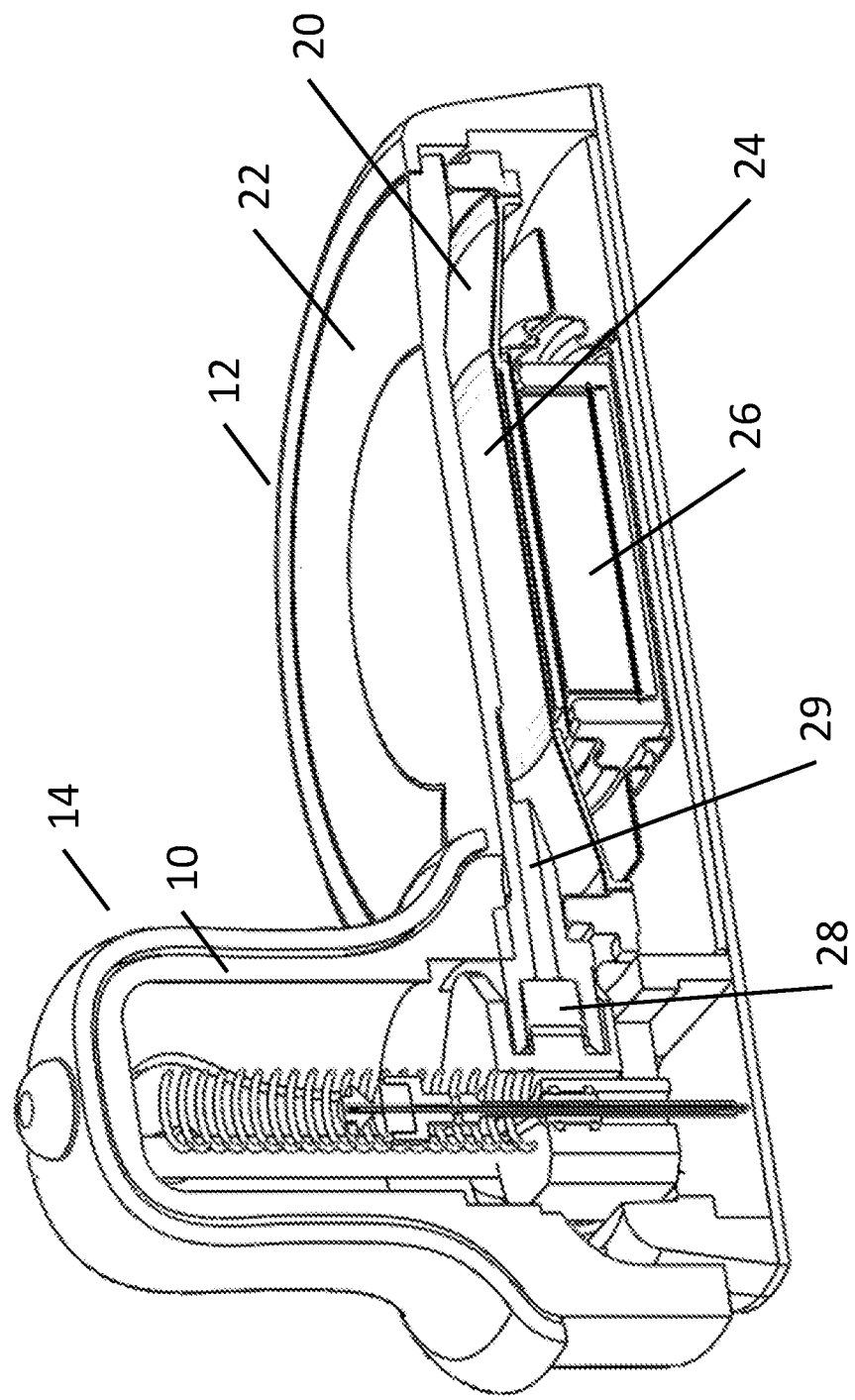

FIGS. 1a and 1b provide exploded and assembled isometric views of an embodied patch-pump incorporating the present invention, respectively;

FIG. 2 provides an isometric cut-away view of the assembled patch-pump showing the prefilled-reservoir and the cannula assembly;

FIGS. 3a and 3b show cross-sectional views of the patch-pump before and after removal of the safety cover;

FIGS. 4a and 4b provide planar cut-away views showing the stages of the opening of the fluid channel as said safety cover is removed.

Figure 5A:
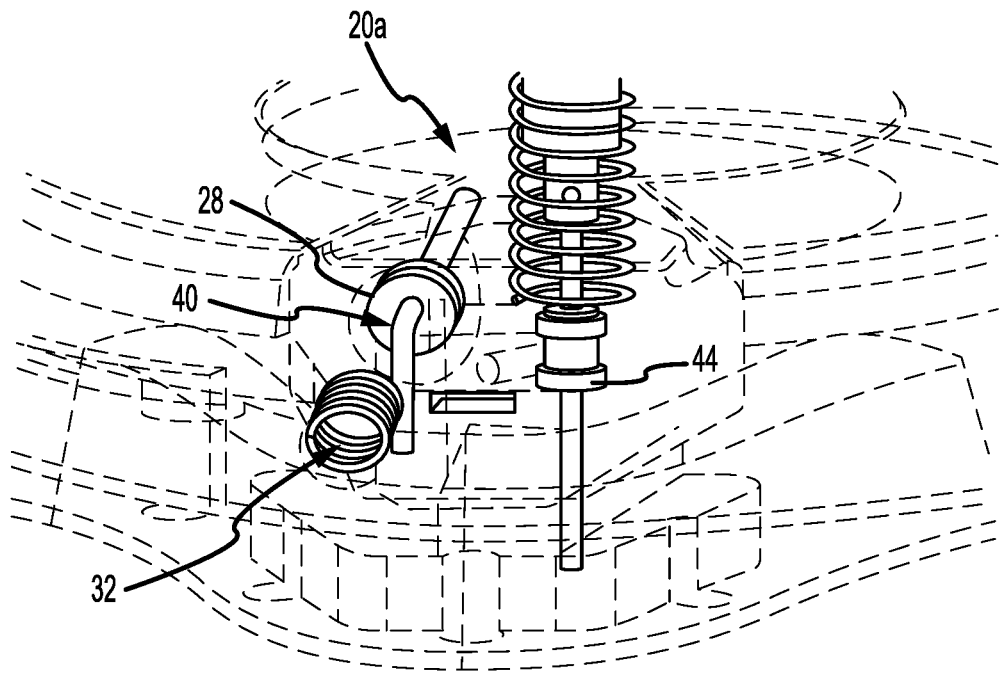
Figure 5B:
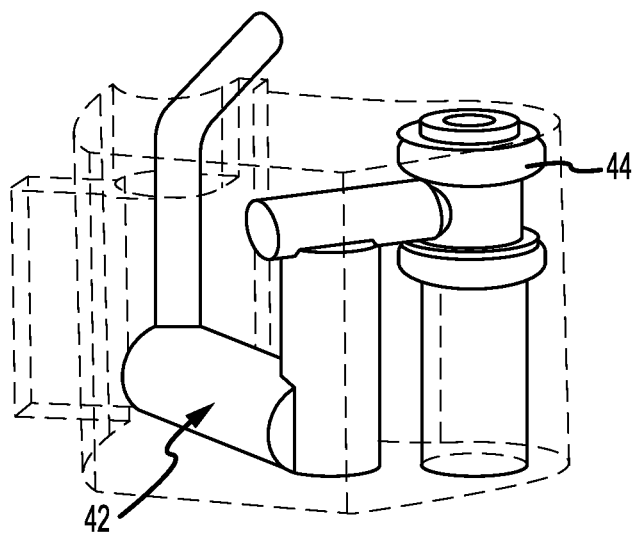

FIGS. 5a and 5b show an embodied orientation and construction/arrangement of a fluid conduit system connecting the drug reservoir-containing element and cannula containing element.

FIGS. 6a, 6b, 6c, 6d, 6e and 6f provide cut-away isometric views of an embodied patch-pump showing the stages of engagement of the elements for penetration of the drug-containing reservoir, activation of the cannula-containing assembly, and potential regulation of the same.

FIGS. 7a, 7b, 7c and 7d depict an embodied patch pump of this invention in various cutaway views, to highlight certain elements of the device, and provide for ease of view of the same.

Figure 8:
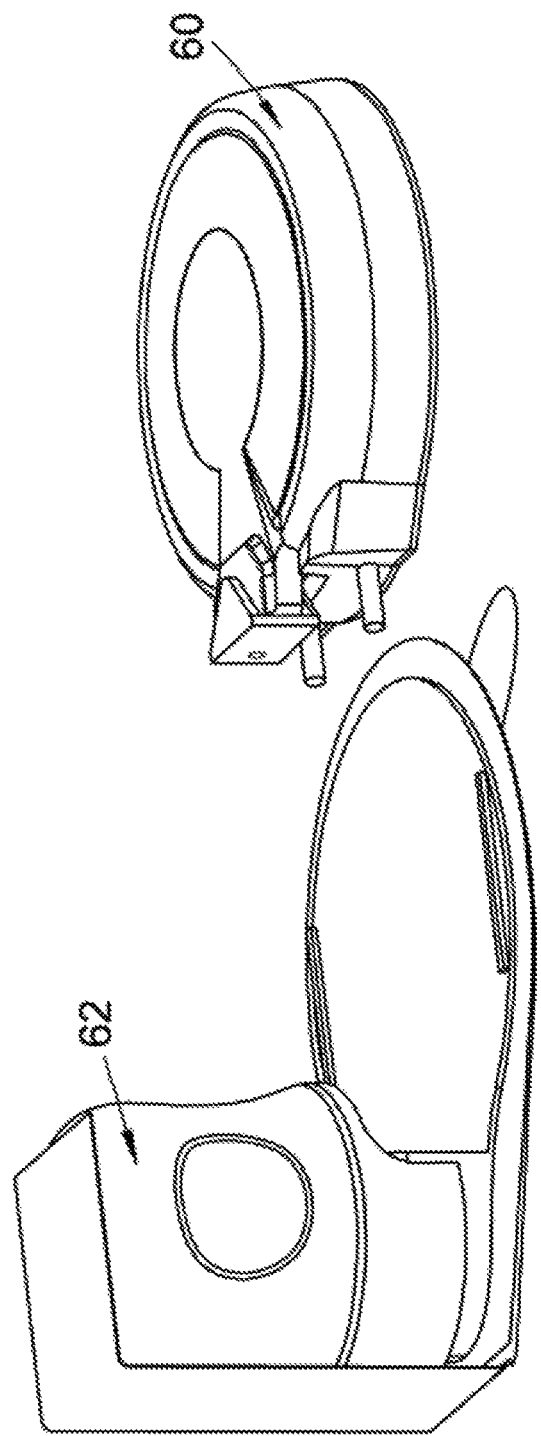

FIG. 8 provides an embodied assembly comprised of operationally connectable units comprised of a drug reservoir-containing unit and a cannula-containing assembly, as opposed to the single unit, depicted in FIGS. 1-6.

DETAILED DESCRIPTION OF THE INVENTION

One embodiment of a patch-pump containing a mechanism of the present invention is shown in exploded form in FIG. 1a, in which a cannula assembly 10, associated with the patch-pump 12, is attached to the housing of the patch-pump as per option c) above. Additionally, in this patch-pump, a safety cover 14 is employed to cover said cannula assembly 10, preventing the inadvertent insertion of the cannula before it is required.

FIG. 1b then shows said patch-pump in its assembled form, it being understood that said safety cover 14 is grasped and removed by the patient immediately prior to activation of the pump.

As will be detailed in connection with the following figures, in this preferred embodiment, removal of this cover 14 initiates the creation of a fluid connection from the drug-reservoir to the cannula.

Referring now to FIG. 2, this cut-away view shows certain component parts of the patch-pump mechanism and how they interact in order to enable the mechanism of the present invention to function in this described embodiment.

According to this aspect, and in one embodiment, a drug is contained within a sealed prefilled drug-reservoir 20, which is formed in the volume between a rigid reservoir wall 22 and a flexible reservoir wall 24. The pump may further comprise an actuator 26, which expands and by doing so moves the flexible wall 24 towards the rigid wall 22; thereby compressing the drug-reservoir 20 in order to expel the drug. The drug reservoir 20 further comprises a septum 28 at the end of a conduit 29 leading from the drug reservoir 20, said septum 28 sealing said reservoir while allowing penetration thereof using a hollow penetrating member.

Referring now to FIG. 3a, this figure shows how, in this preferred embodiment, the safety cover 14 comprises an internal pin 30 which serves to restrain a first spring 32 in its compressed state. FIG. 3b then shows how the removal of said safety cover 14 enables said spring 32 to expand until it hits a stop 34.

Referring now to FIG. 4a, a planar view showing the spring 32 in its compressed state is shown, and then FIG. 4b shows how the release of said spring 32 causes a penetrating-member 40 to pierce said septum 28, emerging in said conduit 29, thereby effecting a fluid connection between the interior of the drug-reservoir 20 and the fluid-passageway 42 leading to the cannula 44. The prefilled drug-reservoir 20 is stationary relative to a central longitudinal axis defined by the assembly containing cannula 44 during penetration of the sealed prefilled drug reservoir 20 by the selectively activatable penetrator (penetrating member 40).

FIG. 5A shows an enlarged side perspective view of the device. The septum 28 and its piercing by the penetrating member 40 are seen in this view. FIG. 5B shows an exploded view of an embodiment of a fluid connection between the interior of the drug reservoir as it enters the fluid passageway 42 and its conveyance to the cannula 44.

Referring now to FIGS. 6a through 6f, the details of how the drug from the fluid-passageway 42 flows through to the interior of the cannula 44 as the cannula is inserted into the body, are shown. In this embodiment, the type of cannula used permits an insertion-needle, which in turn, leads the cannula into its place and can be withdrawn. The steps of this process serve to create the above mentioned fluid connection, as follows.

Figure 6B:
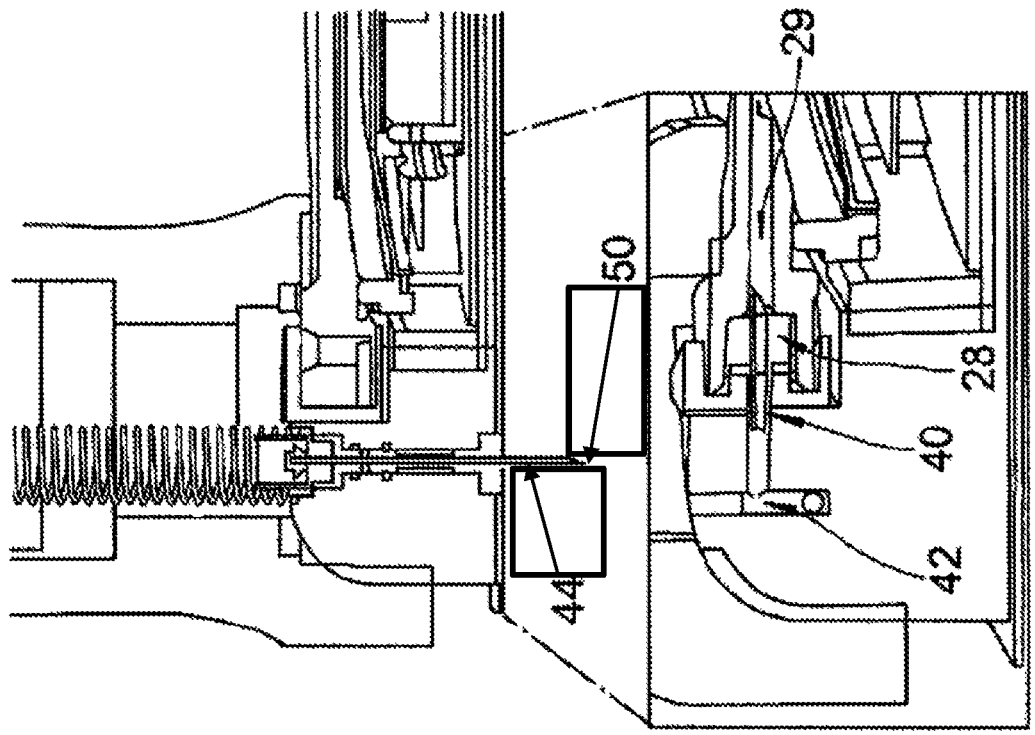
Figure 6A:
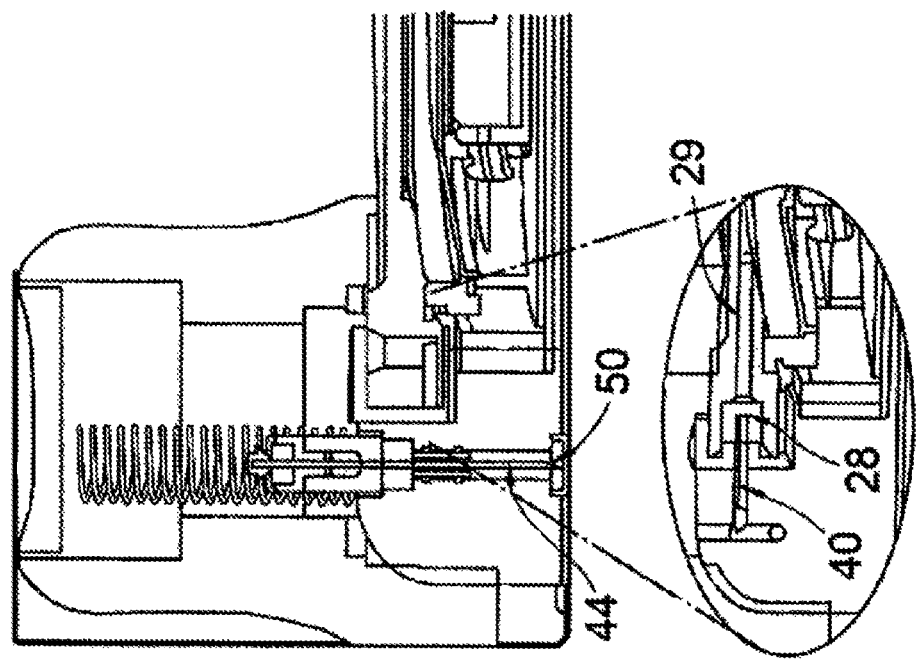

FIG. 6a-6b shows the overall arrangement of the cannula insertion mechanism and its fluid connection to the drug reservoir, including an enlargement of the fluid connection, as shown in the inserts in FIG. 6a and FIG. 6b. In this aspect, the piercing of the septum 28 by the first penetrating member 40, permits fluid exit from the drug reservoir 20 into the fluid passageway 42.

Figure 6D:
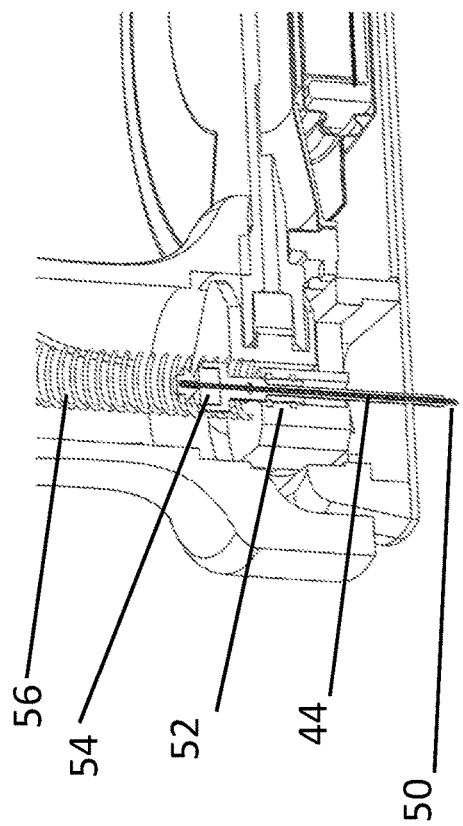
Figure 6F:
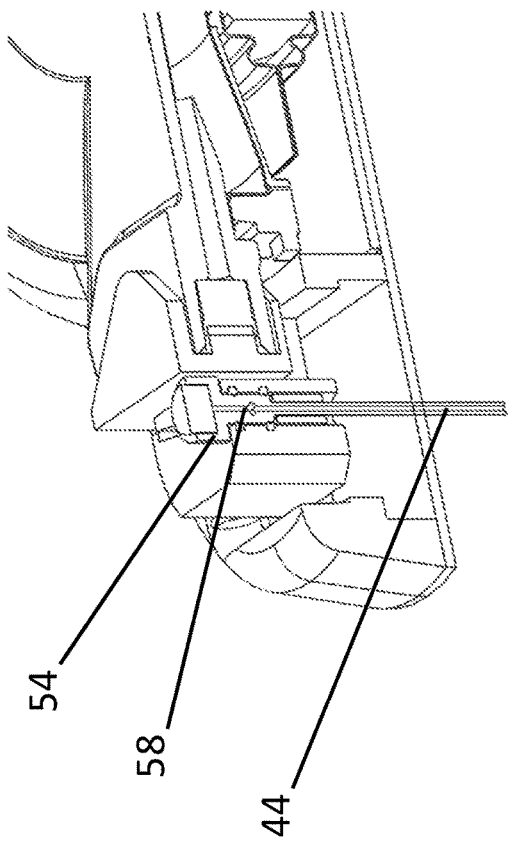
Figure 6C:
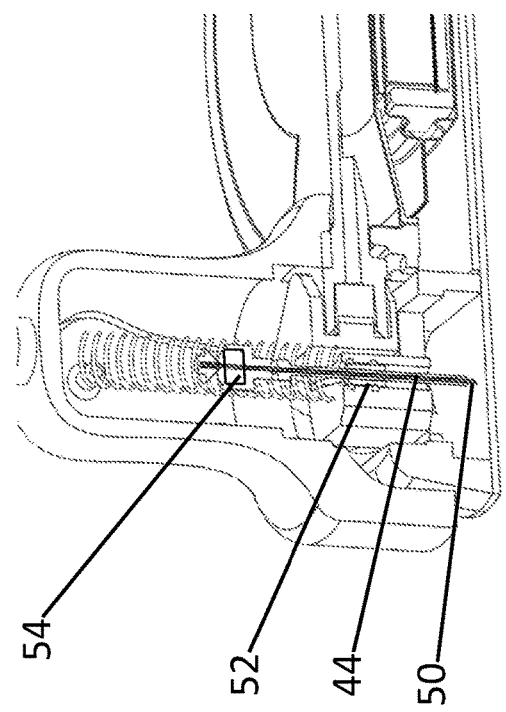
Figure 6E:
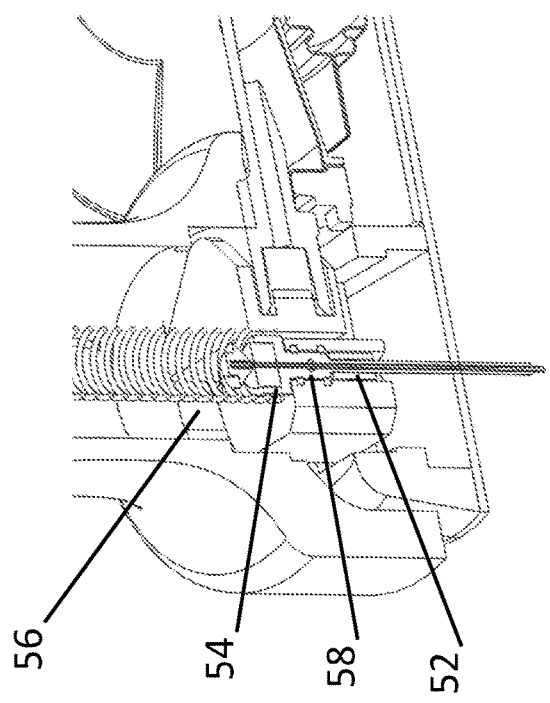
Figure 7A:
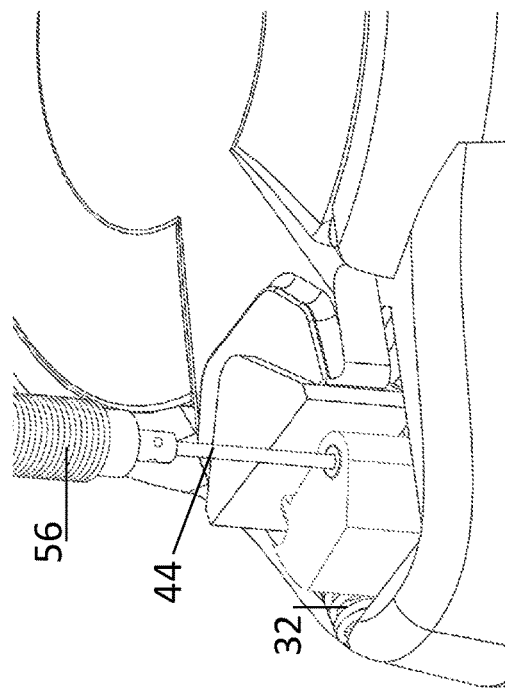
Figure 7B:
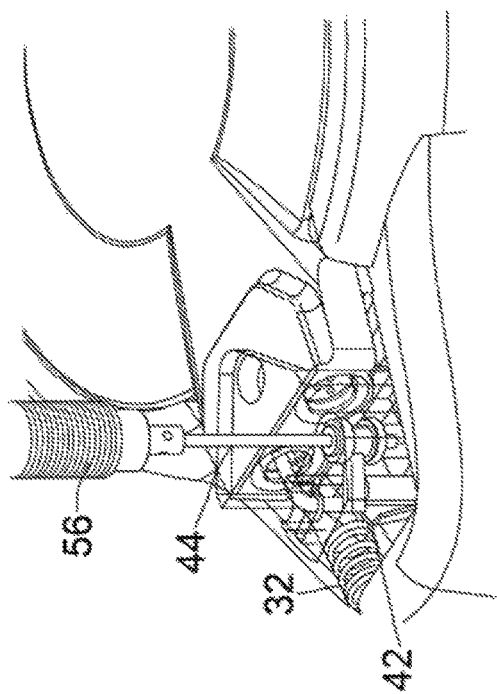
Figure 7C:
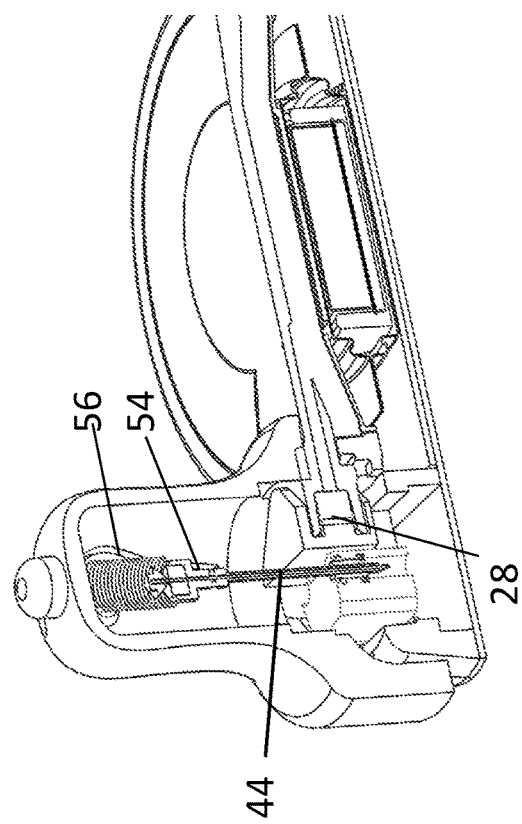
Figure 7D:
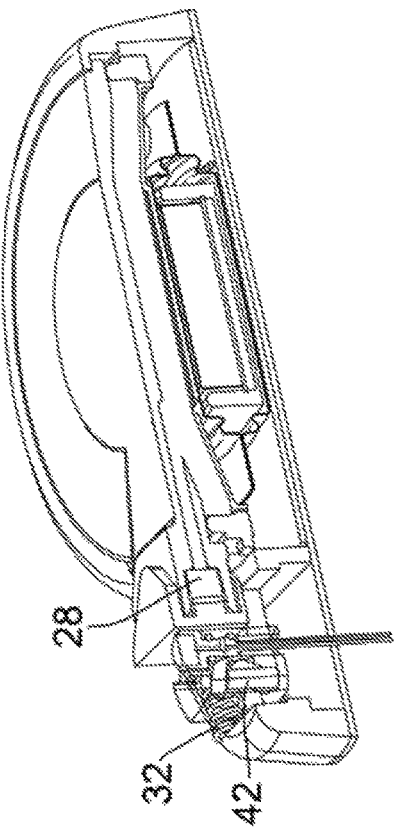

FIG. 6c shows the initial state of the cannula insertion mechanism in which both the insertion-needle 50 and cannula 44 are within the patch-pump. In this initial state, the flow from the passageway 42 (shown in FIG. 6b) is blocked by a plastic sleeve 52, ensuring that none of the drug is lost until the cannula 44 has been inserted under the skin. Referring now to FIG. 6d, the state in which the needle-insertion spring 56 has pressed the cannula-connector 54 down to the point where it comes in contact with the sleeve 52. Note that at this point the tips of the needle 50 and cannula 44 start to emerge from the base of the patch-pump. Referring now to FIG. 6e, the state in which the needle-insertion spring 56 has come to the end of its travel is shown. In this state, cannula-connector 54 has now moved down the sleeve 52 and taken its place. Also visible in this view is the hole 58 in the cannula-connector 54 which is now situated opposite the passageway 42. The final stage in the cannula insertion is now shown in FIG. 5d, in which the cannula-connector 54 has had the needle removed, leaving just the cannula 44 in place. In this state, the hole 58 in the cannula-connector 54 is aligned with the passageway 42 and thus enables flow of the drug from said passageway 42 through to the end of the cannula 44; thereby completing the liquid connection from the pre-filled drug-reservoir all the way to the subcutaneous layer.

FIG. 7 depicts an embodied patch pump of this invention in various cutaway views, to highlight certain elements of the device, and provide for ease of view of the same. FIG. 7a provides a side, cut-away view of the device, showing various elements of the drug insertion mechanism and drug reservoir element and connection between the same, prior to activation of the device. FIG. 7c shows and side and partial top cut away view of the device in FIG. 7a, emphasizing placement of the cannula 44 traversing the device in order to promote penetration of the skin proximally located beneath the device. The relative positioning of the drug reservoir 20, septum 28 and first spring 32 are shown, as well. The conduit 42 in fluid connection with both the drug reservoir and cannula containing assembly is seen, as well. FIGS. 7b and 7d provide line and filled in drawings of the connection between the drug reservoir and cannula containing assembly.

FIG. 8 shows another embodied device of the invention. According to this aspect, the drug reservoir and associated elements 60 are attachable to the drug insertion mechanism 62, in a manner facilitating fluid communication, as in the embodied device in FIGS. 2-6. In this aspect, multiple drug-containing reservoir elements 60 can be attached to the drug insertion means 62.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a," "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A method of delivering a drug, the method comprising:
   removing or releasing a structure from a patch-pump assembly to automatically cause a penetrator to penetrate a sealed prefilled drug-reservoir containing the drug to establish fluid communication between the sealed prefilled drug-reservoir and a fluid-passageway, wherein the patch-pump assembly comprises the sealed prefilled drug-reservoir, the fluid-passageway, a cannula-containing assembly, and the penetrator;
   flowing the drug from the sealed prefilled drug-reservoir to the fluid-passageway;
   flowing the drug from the fluid passageway to the cannula-containing assembly; and
   delivering the drug subcutaneously to a subject using the cannula-containing assembly.

2. The method of claim 1, further comprising:
   preventing inadvertent activation of the patch-pump assembly with the structure.

3. The method of claim 1, further comprising:
   compressing the sealed prefilled drug-reservoir after penetration of the sealed prefilled drug-reservoir.

4. The method of claim 1, wherein
the patch-pump assembly comprises a first spring-based mechanism, and
penetrating the sealed prefilled drug-reservoir comprises releasing a spring of the first spring-based mechanism.

5. The method of claim 1, further comprising puncturing skin of the subject with the cannula-containing assembly before delivering the drug subcutaneously to the subject.

6. The method of claim 1, wherein the penetrator comprises a hypodermic needle.

7. The method of claim 1, wherein the patch-pump assembly is a single unit.

8. The method of claim 1, wherein:
the patch-pump assembly comprises a first spring-based mechanism, and
removing or releasing the structure causes the first spring-based mechanism to propel the penetrator through the fluid-passageway.

9. The method of claim 8, wherein during initiation of penetration and during penetration of the sealed prefilled drug-reservoir, the sealed prefilled drug-reservoir remains stationary relative to a central longitudinal axis defined by the cannula-containing assembly.

10. The method of claim 1, further comprising:
propelling the cannula-containing assembly toward proximally located skin of the subject after flowing the drug to the fluid-passageway.

11. The method of claim 10, further comprising:
aligning an access port of the cannula-containing assembly with the fluid-passageway.

12. The method of claim 11, wherein aligning the access port comprises propelling the cannula-containing assembly to establish drug access from the fluid-passageway to the cannula-containing assembly.

* * * * *